(12) United States Patent
Nelson et al.

(10) Patent No.: US 11,006,882 B2
(45) Date of Patent: May 18, 2021

(54) MEDICAL SENSOR

(71) Applicant: Johnson Electric S.A., Murten (BH)

(72) Inventors: Scott Nelson, Georgetown, MA (US);
Richard Kolenda, Groton, MA (US);
Libing Zhang, Sharon, MA (US)

(73) Assignee: JOHNSON ELECTRIC INTERNATIONAL AG, Murten (CH)

( * ) Notice: Subject to any disclaimer, the term of this patent is extended or adjusted under 35 U.S.C. 154(b) by 333 days.

(21) Appl. No.: 16/010,393

(22) Filed: Jun. 15, 2018

(65) Prior Publication Data

US 2019/0380602 A1    Dec. 19, 2019

(51) Int. Cl.
*A61B 5/24*    (2021.01)
*A61B 5/00*    (2006.01)

(52) U.S. Cl.
CPC .............. *A61B 5/24* (2021.01); *A61B 5/68335* (2017.08); *A61B 2562/164* (2013.01); *A61B 2562/166* (2013.01)

(58) Field of Classification Search
CPC . A61B 5/68335; A61B 5/0416; A61B 5/0408; A61B 5/0444; A61B 5/0478; A61B 5/0492; A61B 5/6613; A61B 5/6814; A61B 5/6815; A61B 5/622; A61B 5/6823; A61B 5/6824; A61B 5/6826; A61B 5/6828; A61B 5/6829; A61B 5/6832; A61B 5/6833
USPC .................................................. 606/391, 392
See application file for complete search history.

(56) References Cited

U.S. PATENT DOCUMENTS

| | | | | |
|---|---|---|---|---|
| 3,828,766 A | * | 8/1974 | Krasnow | A61B 5/0408 600/391 |
| 3,993,049 A | * | 11/1976 | Kater | A61B 5/04085 600/391 |
| 4,050,453 A | * | 9/1977 | Castillo | A61B 5/0408 600/391 |
| 4,370,984 A | * | 2/1983 | Cartmell | A61B 5/04026 600/385 |
| 4,522,211 A | * | 6/1985 | Bare | A61B 5/04087 439/325 |
| 4,653,501 A | * | 3/1987 | Cartmell | A61B 5/04087 600/392 |
| 4,945,911 A | * | 8/1990 | Cohen | A61B 5/0408 600/391 |
| 5,465,715 A | * | 11/1995 | Lyons | A61B 5/04087 600/391 |
| 7,085,598 B2 | * | 8/2006 | Sato | A61B 5/0408 600/372 |

* cited by examiner

*Primary Examiner* — Eun Hwa Kim
(74) *Attorney, Agent, or Firm* — Millman IP Inc.

(57) ABSTRACT

In an aspect, the present disclosure discloses a medical sensor to be connected to a monitoring device for vital sign monitoring. The medical sensor includes a flexible circuit layer having an electrode pattern, a foam layer laminated on the flexible circuit layer, a bonding layer sandwiched between the flexible circuit layer and the foam layer to bond the foam layer with the flexible circuit layer, and a gel sponge disposed on and electrically connected to the electrode pattern through the foam layer and the bonding layer. The area of the bonding layer is smaller than the area of the foam layer. A part of the foam layer adjacent the perimeter is not covered by the bonding layer, and not bonded to the flexible circuit layer by the bonding layer to provide the medical sensor enough conformability to a body.

8 Claims, 3 Drawing Sheets

MEDICAL SENSOR

TECHNICAL FIELD

The present application relates to a medical sensor. More specifically, the present application relates to a medical sensor employing electrode pads as the skin interface to obtain the electrical signals from a human body.

BACKGROUND

Many types of disposable medical sensors are used in vital sign monitoring, such as electrocardiogram (ECG), electroencephalogram (EEG), electromyogram (EMG) monitoring, neuro stimulation and the like.

A medical sensor usually includes a hydrogel acting as the skin interface between the skin and the circuitry of the monitoring device. Traditionally, the circuitry is a button electrode, which is connected to the monitoring device through a cable. Since the button electrode is relatively rigid, the medical sensor lacks flexibility, and is hard to be conformably attached to the skin.

SUMMARY

Therefore, it is an object of the present application to provide a medical sensor with improved conformability to a human body.

Accordingly, in an aspect, the present disclosure provides a medical sensor to be connected to a monitoring device for vital sign monitoring. The medical sensor includes a flexible circuit layer having a substrate and an electrode pattern provided on one of opposite sides of the substrate, a foam layer laminated on the flexible circuit layer, a bonding layer sandwiched between the flexible circuit layer and the foam layer to bond the foam layer with the flexible circuit layer, and a gel sponge disposed on and electrically connected to the electrode pattern. The foam layer and the bonding layer respectively define an opening in alignment with the electrode pattern to enable the gel sponge to be located therein. The area of the bonding layer is smaller than the area of the foam layer. A part of the foam layer adjacent the perimeter is not covered by the bonding layer and not bonded to the flexible circuit layer by the bonding layer.

Preferably, the perimeter of the foam layer falls within the perimeter of the flexible circuit layer.

Preferably, the thickness of the gel sponge is slightly larger than the total thickness of the foam layer and the bonding layer.

Preferably, the electrode pattern is printed on the substrate with conductive ink.

Preferably, the conductive ink is thermoplastic conductive ink.

Preferably, the medical sensor further includes a release liner adhered to a side of the foam layer opposite to the flexible circuit layer.

Preferably, the medical sensor further includes a stiffener disposed on the side of the substrate of the flexible circuit layer opposite to the foam layer and in alignment with the electrode pattern. The stiffener is hard enough to keep the shape of the electrode pattern.

Preferably, the stiffener is substantially the same in size and shape as the electrode pattern.

Preferably, the substrate comprises a substantially circular body portion and a tab extending from the periphery of the body portion to facilitate the user to handle the medical sensor.

Preferably, the flexible circuit layer further includes a plurality of conductive traces provided on the substrate. The substrate includes a substantially circular body portion and a tail portion extending from the periphery of the body portion. The electrode pattern is provided on the body portion, and the plurality of conductive traces are provided on and extending along the tail portion. Opposite ends of the plurality of conductive traces are respectively electrically connected to the electrode pattern and the monitoring device.

BRIEF DESCRIPTION OF THE DRAWINGS

A preferred embodiment of the present application will now be described, by way of example only, with reference to figures of the accompanying drawings. In the figures, identical structures, elements or parts that appear in more than one figure are generally labeled with a same reference numeral in all the figures in which they appear. Dimensions of components and features shown in the figures are generally chosen for convenience and clarity of presentation and are not necessarily shown to scale. The figures are listed below.

DETAILED DESCRIPTION OF EMBODIMENTS

Figure 1:
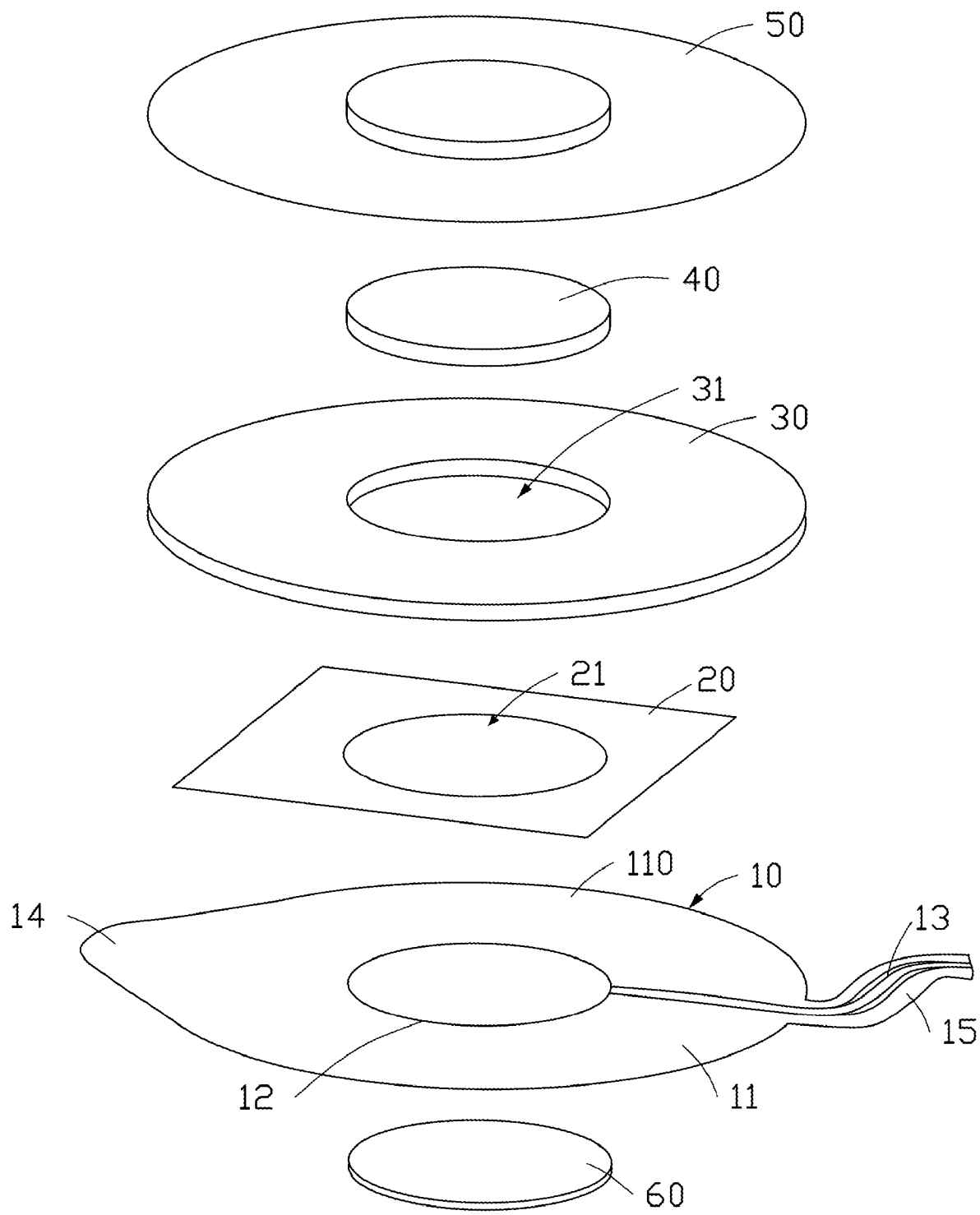
FIG. 1 is an exploded view of a medical sensor according to an embodiment of the present disclosure.

Embodiments of the present application are described below in detail with reference to the drawings. Each drawing merely schematically illustrates the embodiments to allow sufficient understanding of the embodiments. Therefore, the embodiments are not limited to those shown in the drawings. In addition, in each drawing, common and similar components are marked with the same symbols, and duplicative explanations are omitted.

Referring to FIG. 1, a medical sensor 100 in an embodiment of the present disclosure includes a flexible circuit layer 10, a bonding layer 20, a foam layer 30, a gel sponge 40, a release liner 50, and a stiffener 60.

The flexible circuit layer 10 includes a substrate 11, such as a Mylar substrate, an electrode pattern 12 provided on the substrate 11, and a plurality of conductive traces 13 also provided on the substrate 11 and electrically connected to the electrode pattern 12. The electrode pattern 12 and the conductive trace 13 are printed on the substrate 11 with conductive ink. Preferably, the conductive ink is thermoplastic conductive ink for flexibility. The conductive trace 13 can be connected to a monitoring device to make medical sensor 100 electrically connected to the monitoring device, and thereby enabling electrical signals to be transferred between the sensor 100 and the monitoring device.

In one embodiment, the substrate 11 includes a substantially circular body portion 110, and a tab 14 and a tail portion 15 respectively extending from the periphery of the body portion 110. The tab 14 and the tail portion 15 are substantially opposite to each other. The tab 14 facilitates the user to handle the medical sensor 100. The conductive trace 13 is printed on the tail portion 15 and extends along the tail portion 15. It can be understood that the conductive trace 13 is further covered with an insulating layer (not shown). It can be understood that, in another embodiment, the tail portion 15 may be omitted and replaced by a cable to connect the medical sensor 100 to the monitoring device. It can be understood that the tab 14 and the tail portion 15 can be disposed anywhere on the periphery of the substrate 11, and the positions of the two are not necessarily "opposite".

The foam layer 30 is laminated on the flexible circuit layer 10. The side of the foam layer 30 opposite to the flexible circuit layer 10 is coated with skin adhesive, which enables the medical sensor 100 to be attached to the human body. The bonding layer 20 is sandwiched between the foam layer 30 and the flexible circuit layer 10 to bond the foam layer 30 with the flexible circuit layer 10. The foam layer 30 and the bonding layer 20 are respectively provided with openings 31 and 21 in alignment with the electrode pattern 12 on the flexible circuit layer 10. The gel sponge 40 is disposed on the electrode pattern 12 through the openings 31 and 21. Therefore, the gel sponge 40 is electrically connected with electrode pattern 12 to enable physiological signals detected by the gel sponge 40 to be transferred to the monitoring device through the flexible circuit layer 10. The size of the gel sponge 40 is substantially the same as the size of the openings 31 and 21, and the thickness of the gel sponge 40 is slightly larger than the total thickness of the foam layer 30 and the bonding layer 20. In some embodiments, the term "slightly larger than" may mean that the gel sponge 40 is larger than the total thickness of the foam layer 30 by less than about 25%. In other embodiments, the term "slightly larger than" may mean that the gel sponge 40 is larger than the total thickness of the foam layer 30 by an amount that is greater than 25% but less than some other amount. Therefore, after the foam layer 30 is attached to the human body, the gel sponge 40 is subjected to a certain amount of pressure to ensure that the gel sponge 40 is in close contact with the human body. The thickness refers to a distance in the direction of the stacking of the flexible circuit layer 10, the bonding layer 20, and the foam layer 30.

In the direction perpendicular to stacking, the area of the foam layer 30 is smaller than or equal to that of the flexible circuit layer 10. Therefore, the perimeter of the foam layer 30 falls within the perimeter of the flexible circuit layer 10 to protect the foam layer 30 from being damaged or deformed.

In addition, in the direction perpendicular to stacking, the area of the bonding layer 20 is smaller than the area of the foam layer 30. Therefore, a part of the foam layer 30 adjacent the perimeter is not covered by the bonding layer 20, and not bonded to the flexible circuit layer 10. In other words, the area of the foam layer 30 adjacent the perimeter can break away from the bonding layer 20. Therefore, the restriction of the flexible circuit layer 10 to the foam layer 30 is decreased, and the foam layer 30 can be bent easily to provide more conformability to the human body. Preferably, the ratio of the area of the bonding layer 20 to the foam layer 30 is in range of 25%~75%, to make sure the foam layer 30 is firmly bonded to the flexible circuit layer 10, as well as, to provide the medical sensor 100 enough conformability to the human body.

Figure 2:
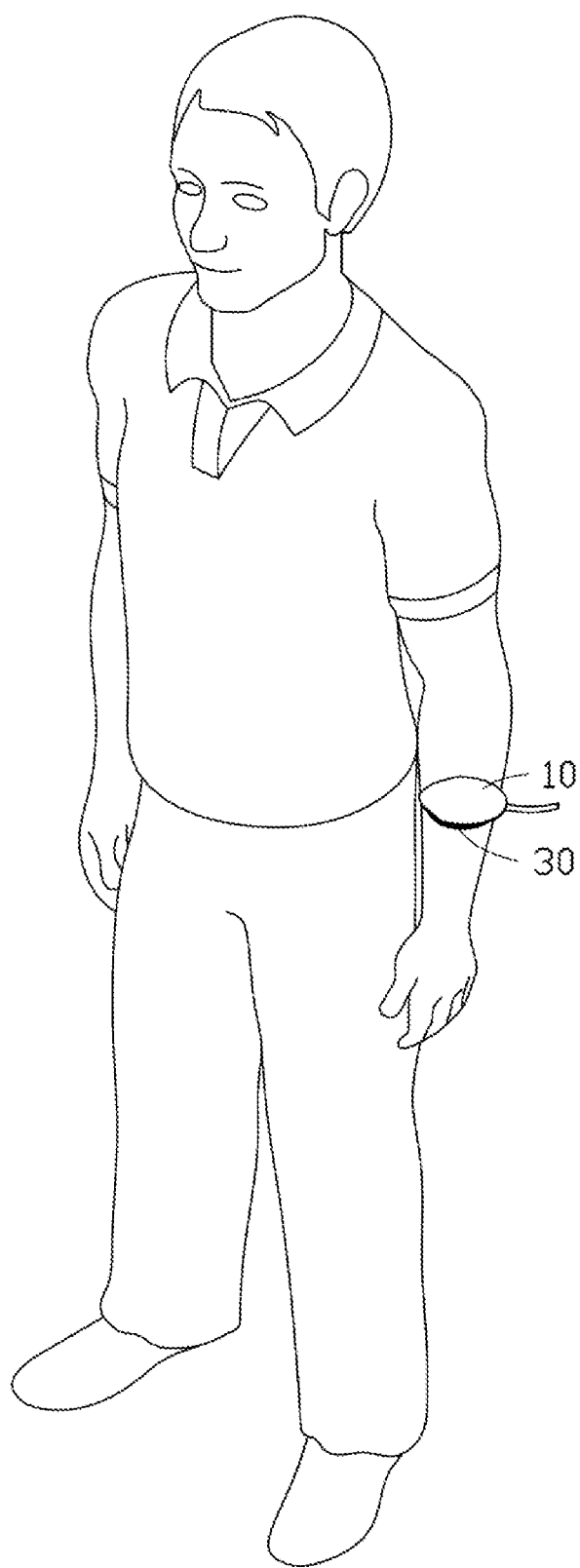
FIG. 2 is a schematic view of the sensor shown in FIG. 1 adhered to a human body.

The release liner 50 is adhered to a side of the foam layer 30 opposite to the flexible circuit layer 10 to protect the foam layer 30 and the gel sponge 40 from being contaminated and damaged. In use, the release liner 50 is peeled off to expose the foam layer 30 and the gel sponge 40, and the foam layer 30 is adhered to the human body. As shown in FIG. 2, since the bonding layer 20 is reduced in size, the conformability of the foam layer 30 is improved to make the foam layer 30 be adapted for the curvature of the human body. The medical sensor 100 can be attached to the human body firmly and comfortably.

The stiffener 60 is hard enough to be used to keep the shape of the electrode pattern 12, i.e. to prevent the medical sensor 100 from being deformed when the medical sensor 100 is adhered to the human body, even if the body has a large curvature. Specifically, in the present embodiment, the stiffener 60 is disposed on the side of the substrate 11 of the flexible circuit layer 10 opposite to the foam layer 30 and in alignment with the electrode pattern 12. In the direction perpendicular to stacking, the stiffener 60 is substantially the same in size and shape as the electrode pattern 12.

It is to be understood that in other embodiments, the thickness of the gel sponge 40 may also be approximately equal to the thickness of the foam layer 30 and the bonding layer 20. There could be two or more electrode patterns 12 on the flexible circuit layer 10. Furthermore, the number of openings 31 and 21 respectively in the foam layer 30 and the bonding layer 20, and the number of gel sponges 40 and stiffeners 60 are also two or more corresponding to the number of the electrode patterns 12.

Figure 3:
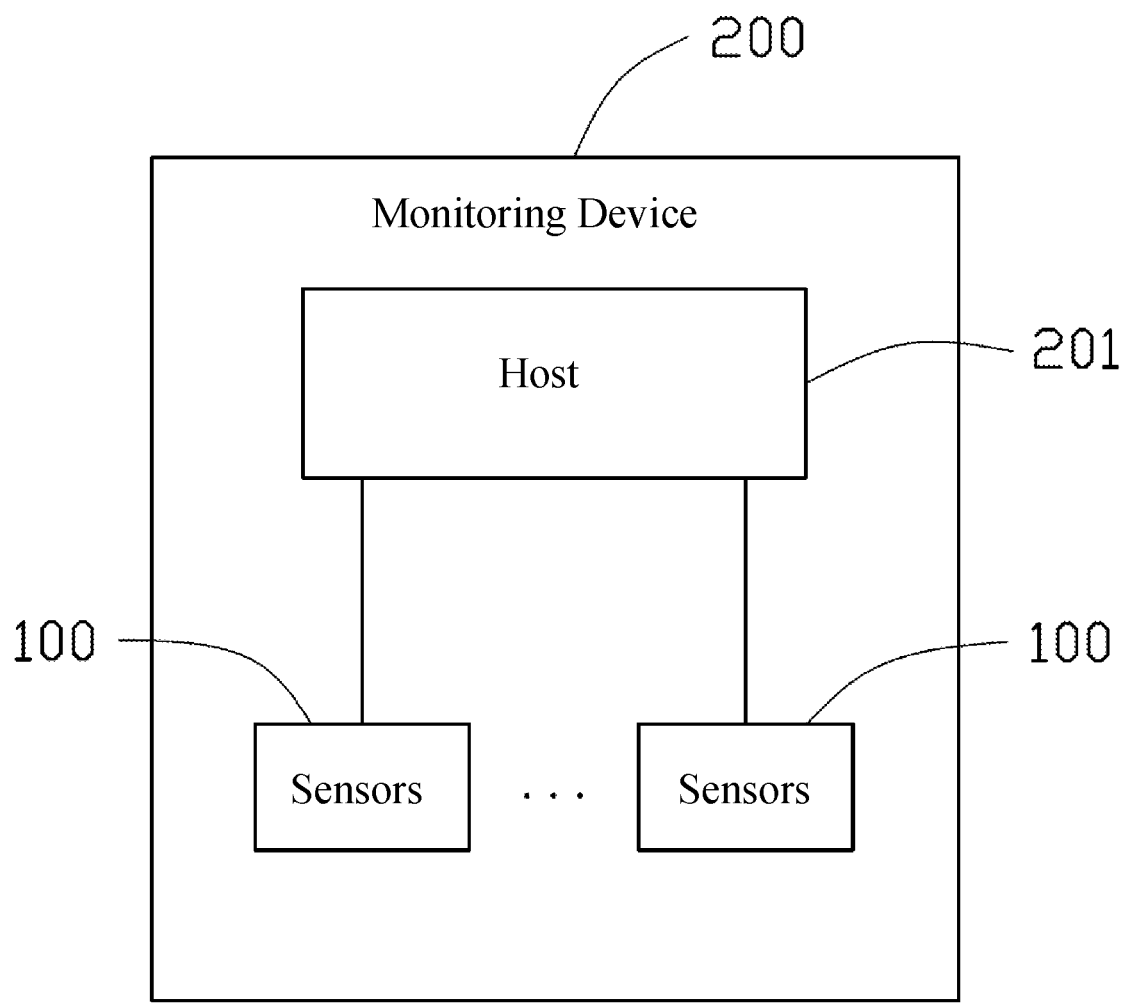
FIG. 3 shows a monitoring device including two or more the medical sensors shown in FIG. 1.

Referring to FIG. 3, a monitoring device 200 to be connected with more than one of the medical sensors 100 is shown. The monitoring device 200 includes a host 201 and a plurality of medical sensors 100 connected to the host 201. In one embodiment, the connection between the host 201 and the medical sensors 100 is a detachable connection, e.g., plugging. The medical sensors 100 collect a physiological signal of the human body and convert it into a corresponding electrical signal. Then the corresponding electrical signal is transferred to the host 201. The host 201 analyses the electrical signal to conduct vital sign monitoring of the human body.

While certain exemplary embodiments have been described and shown in the accompanying drawings, it is to be understood that such embodiments are merely illustrative of and not restrictive on the broad invention, and that this invention should not be limited to the specific construction and arrangement shown and described, since various other modifications may occur to those ordinarily skilled in the art.

What is claimed is:

1. A medical sensor to be connected to a monitoring device for vital sign monitoring, comprising:
   a flexible circuit layer comprising a substrate and an electrode pattern printed on one of opposite sides of the substrate;
   a foam layer laminated on the flexible circuit layer, and defining an opening in alignment with the electrode pattern facing the foam layer;
   a bonding layer sandwiched between the flexible circuit layer and the foam layer to bond the foam layer with the flexible circuit layer, the bonding layer defining an opening in alignment with the opening of the foam layer, wherein the area of the bonding layer is smaller than the area of the foam layer, a part of the foam layer adjacent a perimeter thereof is not covered by the bonding layer, and not bonded to the flexible circuit layer by the bonding layer;
   a gel sponge disposed on the electrode pattern through the openings of the foam layer and the bonding layer to enable the gel sponge to electrically connect to the electrode pattern;
      wherein the area of the foam layer is smaller than or equal to that of the flexible circuit layer, in a direction perpendicular to a stacking thereof, and the flexible circuit layer completely overlies the foam layer.

2. The medical sensor of claim 1, wherein outer perimeter of the foam layer falls within outer perimeter of the substrate of the flexible circuit layer.

3. The medical sensor of claim 1, wherein the thickness of the gel sponge is slightly larger than the total thickness of the foam layer and the bonding layer.

4. The medical sensor of claim 1, further comprising a release liner adhered to a side of the foam layer opposite to the flexible circuit layer.

5. The medical sensor of claim 1, further comprising a stiffener disposed on the side of the substrate of the flexible circuit layer opposite to the foam layer and in alignment with the electrode pattern, wherein the stiffener is hard enough to keep the shape of the electrode pattern.

6. The medical sensor of claim 5, wherein the stiffener is substantially the same in size and shape as the electrode pattern.

7. The medical sensor of claim 1, wherein the substrate includes a substantially circular body portion and a tab extending from a periphery of the body portion to facilitate a user to handle the medical sensor.

8. The medical sensor of claim 1, wherein the flexible circuit layer further includes a plurality of conductive traces provided on the substrate, the substrate includes a substantially circular body portion and a tail portion extending from a periphery of the body portion, the electrode pattern is provided on the body portion, the plurality of conductive traces are provided on and extending along the tail portion, and the plurality of conductive traces is adapted to be electrically connected to the monitoring device.

\* \* \* \* \*